United States Patent [19]
Yamaguchi et al.

[11] 4,292,849
[45] Oct. 6, 1981

[54] METHOD FOR CORRECTING THE SENSITIVITY OF AN ELECTROMAGNETIC ULTRASONIC PROBE

[75] Inventors: Hisao Yamaguchi, Akashi; Kazuo Fujisawa, Nishinomiya, both of Japan

[73] Assignee: Sumitomo Metal Industries, Ltd., Osaka, Japan

[21] Appl. No.: 104,462

[22] Filed: Dec. 17, 1979

[30] Foreign Application Priority Data

Mar. 28, 1979 [JP] Japan .................................. 54-37553

[51] Int. Cl.³ ........................................... G01N 29/00
[52] U.S. Cl. ..................................................... 73/643
[58] Field of Search ........................................... 73/643

[56] References Cited

U.S. PATENT DOCUMENTS

3,786,672 1/1974 Gaerttner ............................. 73/643

OTHER PUBLICATIONS

J. Krautkramer et al.; *Ultrasonic Testing of Materials*, pp. 156–163. 1977.

*Primary Examiner*—Stephen A. Kreitman
*Attorney, Agent, or Firm*—Wenderoth, Lind & Ponack

[57] ABSTRACT

Sensitivity of an electromagnetic ultrasonic probe for transmission-reception or for reception is maintained at a fixed level by first obtaining the relationship between the resonance frequency and the transmission-reception sensitivity in the range between the maximum and the minimum lift-offs and then electrically creating a relationship therebetween having an inverse frequency-sensitivity characteristic to said frequency-sensitivity characteristic and electrically adding said two relationships together.

1 Claim, 7 Drawing Figures

METHOD FOR CORRECTING THE SENSITIVITY OF AN ELECTROMAGNETIC ULTRASONIC PROBE

BACKGROUND OF THE INVENTION

The present invention relates to a method for correcting the sensitivity of an electromagnetic ultrasonic probe and, more particularly, to a method for correcting the flaw detection sensitivity so that it is maintained at a fixed value when the distance between the electromagnetic ultrasonic probe and the material to be inspected varies.

In nondestructive testing, recently, ultrasonic flaw detection has been widely used because of its simple handling and high reliability. This flaw detecting method was usually applied to inspection of cold material. Recently, however, it has been found that this method is applicable to surface and internal flaw detection and measurement of the thickness of hot steel material during hot working operation. Since then, the ultrasonic flaw detecting method has also had practical application in use for inspecting hot steel for the purpose of the improvement of quality control and the economy of energy useage.

The following two methods are possible in ultrasonic flaw detection:

(1) ultrasonic waves are generated in a hot steel material by heat shock by heat irradiation of the material using a laser beam and received by an electromagnetic ultrasonic probe; and (2) ultrasonic waves are generated in a hot steel material by an electromagnetic ultrasonic probe and received by the same probe.

In the flaw detection using the electromagnetic ultrasonic probe, the material being inspected is not in direct contact with the probe but is spaced therefrom by a distance (hereinafter called lift-off) of 0.5–3 mm. Eddy currents are generated on the surface of the material being tested, by passing a high frequency pulse current to a coil of the probe. A vibrating force is generated on the surface of the material being inspected by Lorentz's force due to the static magnetic field on the top surface of the material and by the interaction of a magnet of the probe and the eddy current, thereby generating ultrasonic waves having a high frequency. The ultrasonic waves are propagated through the material being inspected, reflected by any source of reflection, and received as electric signals by the electromagnetic ultrasonic probe for reception.

Since the electromagnetic ultrasonic probe can produce sound waves which are different in their mode of vibration by changing the direction of the static magnetic field, it is possible to select a suitable type of vibration for the shape and direction of the defect.

In the ultrasonic flaw detection in which the electromagnetic ultrasonic probe is used for the detection of defects, it is essential that the flaw detection is performed with the initially determined reference sensitivity to the completion of the inspection. For this purpose, the lift-off must be maintained constant throughout the inspection. However, one of the problems encountered in the conventional ultrasonic flaw detection method was that it was impossible to maintain the lift-off constant and, accordingly, it was impossible to detect flaws with the same sensitivity because of the rough surface of the material being inspected, allowable error of the transfer line, and the scales attached thereto.

Accordingly, an object of the present invention is to provide a method for, even when the lift-off varies, correcting the flaw detection sensitivity to always maintain the initial reference sensitivity so as to always perform flaw detection at a constant sensitivity.

SUMMARY OF THE INVENTION

The method for correcting the sensitivity of an electromagnetic ultrasonic probe, according to the present invention using the electromagnetic ultrasonic probe for transmission and reception or for reception, is characterized by obtaining the relationship between resonance frequency and transmission-reception sensitivity between the expected maximum and the minimum lifts-off of said electromagnetic ultrasonic probe, creating electrically a relationship having a frequency-sensitivity characteristic which is an inverse of said relationship, and adding electrically said two relationships together to thereby obtain a constant flaw detection sensitivity.

In the method according to the present invention, the relationship having the frequency-sensitivity characteristic described above is effected by a frequency filter and an amplifier.

In other words, the sensitivity reduced by the increased lift-off is increased by the frequency filter and the amplifier.

BRIEF DESCRIPTION OF THE DRAWINGS

The invention will be better understood from the following description taken in connection with the accompanying drawings in which.

DESCRIPTION OF THE PREFERRED EMBODIMENTS

Figure 2:
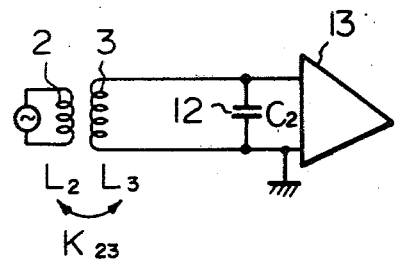
FIG. 2 is a schematic diagram of an equivalent circuit on the reception side of the electromagnetic ultrasonic probe.
Figure 1:
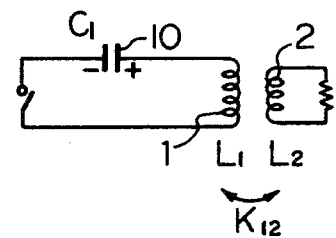
FIG. 1 is a schematic diagram of an equivalent circuit on the transmission side of the electromagnetic ultrasonic probe.

With reference now to the accompanying drawings, preferred embodiments of the present invention will be described. FIGS. 1 and 2 schematically illustrate equivalent circuits on the transmission side and on the reception side, respectively, of the electromagnetic ultrasonic probe.

In FIG. 1, reference character $C_1$ denotes capacity (in farads) of a capacitor 10 as a source of high frequency pulse current, $L_1$ denotes inductance (in henrys) of a transmitter coil 1, $L_2$ denotes inductance (in henrys) by eddy currents 2 induced in a material to be inspected, and $K_{1\,2}$ denotes coupling coefficient between the inductances $L_1$ and $L_2$. Then, the resonance frequency f (Hz) is given by the following equation:

$$f = \frac{1}{2\pi \sqrt{(1 - K_{1\,2}^2) L_1 C_1}} \quad (1)$$

where $0 < K_{1\,2} < 1$

Figure 3:
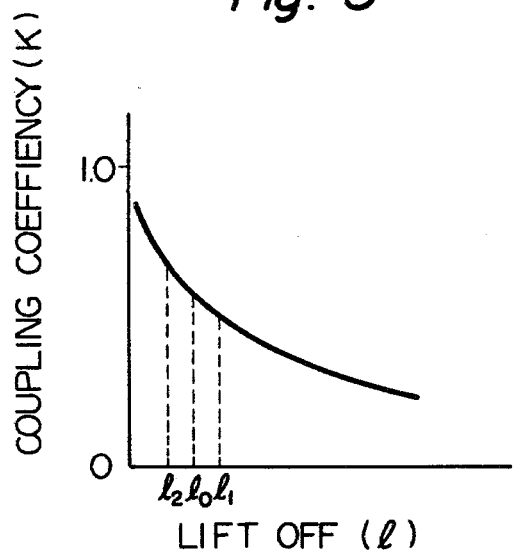
FIG. 3 is a graph showing the relationship between the lift-off and the coupling coefficient.

In this equation, the greater the coupling coefficient $K_{1\,2}$ is, the greater becomes the resonance frequency f. If the inductances $L_1$ and $L_2$ are electromagnetically completely coupled, the coupling coefficient is 1, that is, as the lift-off approaches zero the coupling coefficient $K_{1\,2}$ approaches one. In other words, the greater the lift-off is, the smaller becomes the coupling coefficient $K_{1\,2}$ and, accordingly, the resonance frequency f becomes the smaller. Contrary to this, the smaller the lift-off is, the greater becomes the coupling coefficient $K_{1\,2}$ and, accordingly, the resonance frequency f becomes the greater. The relationship between the lift-off and the coupling coefficient $K_{1\,2}$ is generally as shown in FIG. 3, in which reference characters $l_1$, $l_0$ and $l_2$ denote the expected greatest, the mean and the smallest values of the lift-off, respectively.

In an equivalent circuit on the reception side shown in FIG. 2, having the same function as that on the transmission side, reference character $L_3$ denotes inductance (in henrys) of a receiver coil 3, $C_2$ denotes capacity (in farads) of a capacitor 12 of a receiver circuit, and $K_{2\,3}$ denotes coupling coefficient between the inductances $L_2$ and $L_3$. Then, the resonance frequency f (Hz) if given by the following equation:

$$f = \frac{1}{2\pi \sqrt{(1 - K_{2\,3}^2) L_2 C_2}} \quad (2)$$

where $0 < K_{2\,3} < 1$

The relationship between the lift-off and the coupling coefficient $K_{2\,3}$ is, similar to that of the equivalent circuit on the transmission side, as shown in FIG. 3.

Figure 4:
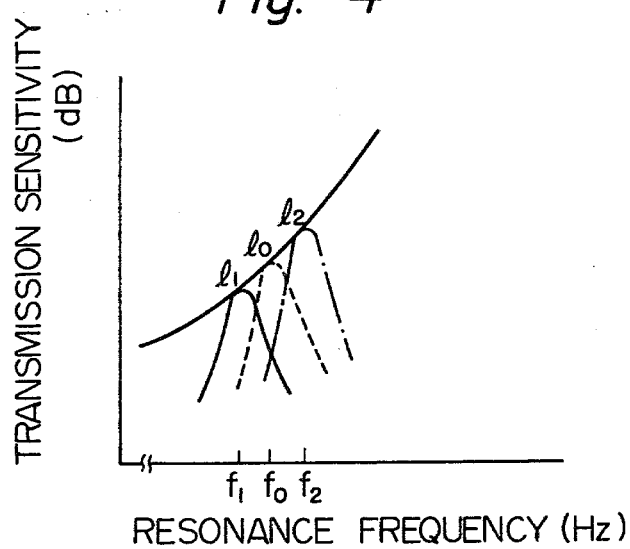
FIG. 4 is a graph showing the relationship between the transmission sensitivity and the resonance frequency at various lift-offs.
Figure 5:
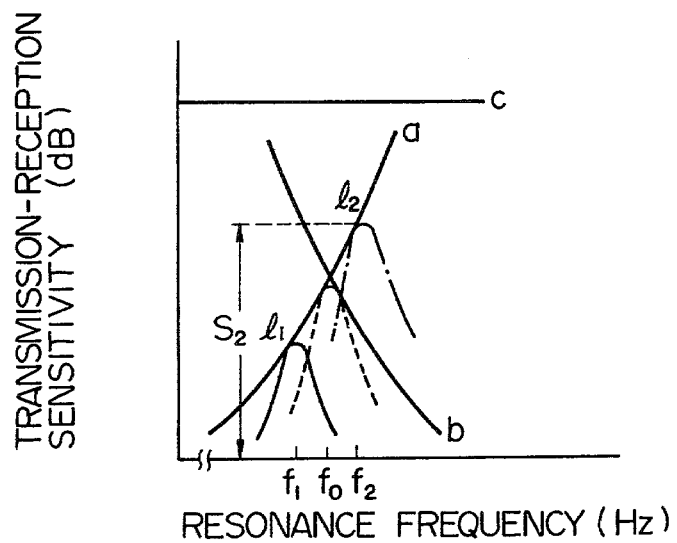
FIG. 5 is a graph showing the relationship between the transmission-reception sensitivity and the resonance frequency and the method for correcting it.
Figure 6:
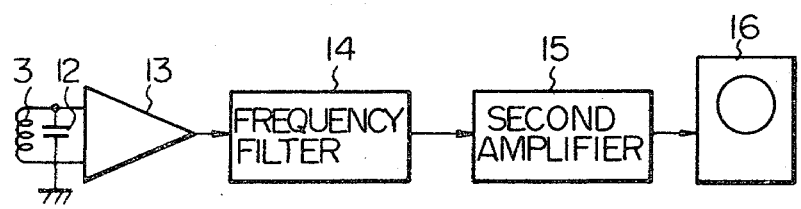
FIG. 6 is a circuit diagram of an embodiment of the method according to the present invention.

Denoting resonance frequencies at the lifts-off $l_1$, $l_0$ and $l_2$ ($l_1 > l_0 > l_2$) by $f_1$, $f_0$ and $f_2$, respectively, there is a relationship $f_1 < f_0 < f_2$ as obvious from the relationship expressed by equation (1) and, accordingly, the relationship between the resonance frequency and the transmission sensitivity on the transmission side is generally as shown in FIG. 4. Likewise, the relationship between the resonance frequency and the transmission-reception sensitivity both on the transmission and the reception sides is shown by curve a of FIG. 5. As obvious from FIGS. 4 and 5, the transmission-reception sensitivity is influenced considerably by the lift-off. The unit dB (decibel) expressing the magnitude of the transmission-reception sensitivity in FIGS. 4, 5 and 6, is defined as 20 log $S'/S_o'$, where $S_o'$ denotes reference sensitivity and $S'$ denotes sensitivity. The magnitude of the sensitivity is usually expressed and compared usually in dB.

In the conventional transmission-reception circuit, as described above, the received signal is amplified by an amplifier 13 under the condition that the transmission-reception sensitivity is varied as the lift-off is varied.

The method for maintaining constant the transmission-reception sensitivity dependent upon the variation in the lift-off according to the present invention will now be described hereinunder in detail. It is assumed here that the curve a of FIG. 5 expresses the interrelationship between the transmission-reception sensitivity and the resonance frequency and that the reference characters $l_1$, $l_2$ and $l_0$ denote the maximum lift-off, the minimum lift-off during flaw detection and the arithmetical mean thereof, respectively and the resonance frequencies thereof are denoted by the reference characters $f_1$, $f_2$ and $f_0$, respectively. In order to maintain the sensitivity constant throughout the inspection it is required to compensate for the variation in the sensitivity due to the variation in the lift-off. This compensation is accomplished by adding the curve a and a curve b to each other, said curve b having a frequency-sensitivity characteristic which is completely inverse to that of the curve a, that is, the curve b has the sensitivity characteristic such that the higher the resonance frequency is, the lower becomes the sensitivity. Then, the flaw detection sensitivity assumes the level expressed by a straight line C formed by addition of said two curves a and b. Thus, it is possible to perform flaw detection with a constant sensitivity at any point between the lifts-off $l_1$ and $l_2$, namely between the resonance frequencies $f_1$ and $f_2$.

An example of the concrete method for providing the curve b may be of a circuit construction shown in FIG. 6, in which a frequency filter 14 and a second amplifier 15 are disposed following the existing amplifier 13 in the circuit of the probe on the reception side so that an output of the second amplifier is applied to a cathode-ray tube oscillograph 16.

To practice the method according to the present invention, the maximum and the minimum lifts-off $l_1$ and $l_2$, respectively, during the flaw detection are first predetermined, and the resonance frequencies $f_1$ and $f_2$ for these lifts-off, respectively, and their transmission-reception sensitivity are determined by, for example, measuring echoes from the bottom surface. That is, the curve a of FIG. 5 is determined prior to the beginning of the flaw detection. If the flaw detecting operation is started at this condition, however, the lift-off during the operation will vary between $l_1$ and $l_2$ and the flaw detection sensitivity will decrease as the lift-off increases. In order to eliminate the variation of the sensitivity and to maintain the sensitivity at the constant level C (dB), it is required to add electrically to the curve a the curve b having the completely inverse frequency-sensitivity characteristic with respect to the curve a.

An electric circuit for applying the curve b is adapted to use the frequency filter 14, designed to have the frequency-sensitivity characteristic expressed as the curve b, and the second amplifier 15. For example, when the maximum lift-off is $l_1$, since the resonance frequency therefor is $f_1$ the sensitivity decreases before the filter 14. However, the sensitivity is amplified as much as $S_2$ (dB) by the filter 14 and the second amplifier 15, thereby making it possible to maintain the predetermined reference sensitivity C (dB). Thus, in the method according to the present invention, it is possible to correct for the variation in the sensitivity between the lifts-off $l_1$ and $l_2$ by means of the frequency filter 14 and the amplifier 15 to maintain the sensitivity at a constant value.

An example of the practice of the method according to the present invention will now be described. A carbon steel sheet of 200 mm thickness was heated to 600° C.–1200° C. and then subjected to normal beam testing from the outer surface thereof. An electromagnetic ultrasonic probe having frequency $f_0 = 1$ MHz ($1 \times 10^6$ Hz) was used both for transmission and for reception. The maximum and the minimum lifts-off were 1.5 mm and 0.5 mm, respectively, and the resonance frequencies therefor were 0.9 MHz ($0.9 \times 10^6$ Hz) and 1.1 MHz ($1.1 \times 10^6$ Hz), respectively. The relationship between the resonance frequency and the transmission-reception sensitivity in the range between the maximum and the minimum lifts-off was as shown by curve A of FIG. 7. According to FIG. 7, the difference in the transmission-reception sensitivity in the range between the maximum and the minimum lifts-off was 10 dB. Assuming here that the transmission-reception sensitivity for the minimum lift-off is 1, the transmission-reception sensitivity for the maximum lift-off is 0.33.

Figure 7:
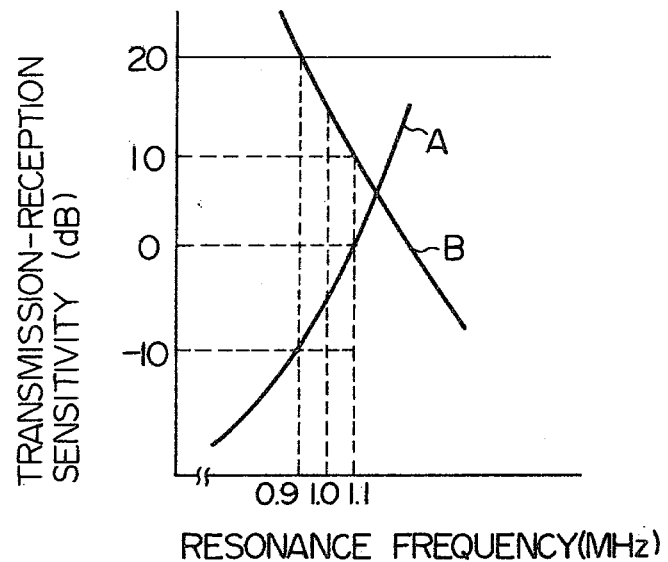
FIG. 7 is a graph showing the relationship between the transmission-reception sensitivity and the resonance frequency in the embodiment of FIG. 6 and the method for correcting it.

In order to eliminate the difference in the sensitivity by the method according to the present invention, the probe circuit on the reception side shown in FIG. 6 was provided with the second amplifier 15 equipped before it with the frequency filter 14 to amplify the sensitivity as shown by a curve B of FIG. 7 so as to maintain the sensitivity at the predetermined constant value in the lift-off range from 0.5 mm to 1.5 mm. As the result, flaw detection was performed substantially without any difference in the sensitivity.

As described above, by the practice of the method according to the present invention it is made possible to perform flaw detection with a constant sensitivity even when the lift-off is varied during the flaw detection and to render a proper judgment of the detected flaw.

In the above-described example, the electromagnetic ultrasonic probe was used both for transmission and for reception. However, those skilled in the art will readily realize that, even when the electromagnetic ultrasonic probe is used only for reception, the practice of the method according to the present invention can eliminate the difference in the flaw detection sensitivity due to the variation in the lift-off.

While we have described and illustrated a present preferred example of practicing the method according to the present invention, it is to be distinctly understood that the invention is not limited thereto but may be otherwise variously practiced within the scope of the following claim.

What is claimed is:

1. In ultrasonic flaw detection using an electromagnetic ultrasonic probe for both transmission and reception or for only reception, a method for correcting the sensitivity of the electromagnetic ultrasonic probe, comprising the steps of:

previously obtaining the relationship between resonance frequency and transmission-reception sensitivity in the range between the maximum and the minimum lifts-off of said electromagnetic ultrasonic probe;

creating electrically a relationship therebetween having an inverse sensitivity-frequency characteristic to said relationship; and adding said two relationships together, thereby obtaining a constant reference sensitivity;

wherein said correction of the sensitivity is performed by an amplifier which is added to a circuit on the reception side of said electromagnetic ultrasonic probe and wherein a frequency filter is disposed before said amplifier.

* * * * *